United States Patent [19]

Varasi et al.

[11] Patent Number: 5,783,574
[45] Date of Patent: Jul. 21, 1998

[54] IMIDAZOLYLAKYL DERIVATIVES OF IMIDAZO [5,1-C][1,4]BENZOXAZIN-1-ONE PROCESS FOR THEIR PREPARATION

[75] Inventors: Mario Varasi, Milan; Franco Heidempergher, Parabiago; Carla Caccia, Gallarate; Patricia Salvati. Arese, all of Italy

[73] Assignee: Pharmacia & Upjohn S.p.A., Milan, Italy

[21] Appl. No.: 578,549

[22] PCT Filed: May 2, 1995

[86] PCT No.: PCT/EP95/01650

§ 371 Date: Jan. 24, 1996

§ 102(e) Date: Jan. 24, 1996

[87] PCT Pub. No.: WO95/32208

PCT Pub. Date: Nov. 30, 1995

[30] Foreign Application Priority Data

May 25, 1994 [GB] United Kingdom ............... 9410469

[51] Int. Cl.$^6$ ............... C07D 498/04; A61K 31/535
[52] U.S. Cl. ............... 544/230.2; 544/101
[58] Field of Search ............... 544/101; 514/230.2

[56] References Cited

U.S. PATENT DOCUMENTS

| | | | |
|---|---|---|---|
| 5,364,854 | 11/1994 | Varasi et al. | 514/230 |
| 5,610,158 | 3/1997 | Bisaha | 544/101 |

FOREIGN PATENT DOCUMENTS 1533020   11/1978   United Kingdom.

OTHER PUBLICATIONS

Melloni et al, *Farmaco*, New 2-substituted 2,3,3a, 4-tetrahydro-1H-imidazo . . ., vol. 46, No. 9, 1991, pp. 1011-1021.

Banzatti et al, *Journal of Heterocyclic Chemistry*, Derivatives of imidazo (5,1-c)(1,4)benzoxazin-1-ones . . ., vol. 20, No. 1, 1983, pp. 130-144.

*Primary Examiner*—Donald G. Daus
*Attorney, Agent, or Firm*—Nikaido Marmelstein Murray & Oram LLP

[57] ABSTRACT

Novel 5-HT$_3$ receptor antagonist compounds having following formula (I)

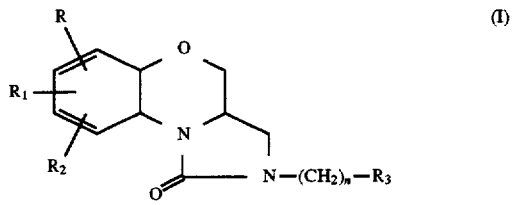

wherein n is 1, 2 or 3;

each of R, R$_1$ and R$_2$, which may be the same or different, is hydrogen, halogen, hydroxy, cyano, C$_1$-C$_6$ alkyl, CF$_3$, C$_1$-C$_6$ alkoxy, C$_1$-C$_6$ alkylthio, formyl, C$_2$-C$_6$ alkanoyl, carboxy, C$_1$-C$_6$ alkoxy-carbonyl, nitro, —N (R$_4$ R$_5$) in which each of R$_4$ and R$_5$ independently is hydrogen, C$_1$-C$_6$ alkyl, formyl or C$_2$-C$_6$ alkanoyl; or a (R$_6$ R$_7$) N—SO$_2$ group, in which each of R6 and R$_7$ independently is hydrogen or C$_1$-C$_6$ alkyl;

R$_3$ is an imidazolyl group of formula

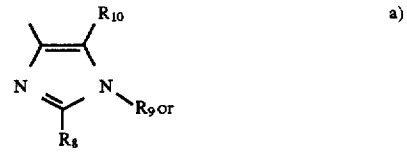

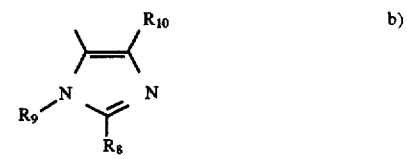

wherein each of R$_8$ and R$_{10}$ which may be the same or different is hydrogen or C$_1$-C$_6$ alkyl, R$_9$ is hydrogen, C$_1$-C$_6$ alkyl or a nitrogen protecting group; and the pharmaceutically acceptable salts thereof, are disclosed.

6 Claims, No Drawings

IMIDAZOLYLAKYL DERIVATIVES OF IMIDAZO [5,1-C][1,4]BENZOXAZIN-1-ONE PROCESS FOR THEIR PREPARATION

This application is a national stage entry of PCT application Ser. No. PCT/EP95/01650, filed on May 2, 1995.

The present invention relates to new imidazolylalkyl derivatives of 2,3,3a,4-tetrahydro-1H-imidazo[5,1-c]-[1,4] benzoxazin-1-one, to a process for their preparation, to pharmaceutical compositions containing them and to their use as therapeutic agents.

Imidazo-benzoxazin derivatives active on the CNS are already described in the prior-art, for instance in U.S. Pat. No. 4,134,974 and in WO93/25555. In particular the broad general chemical formula disclosed by U.S. Pat. No. 4,134,974 embraces also 1-imidazolyl derivatives of imidazo[5,1-c]-[1,4]benzoxazin-1-one compounds.

The present invention provides novel compounds having following formula (I)

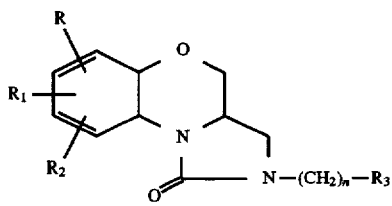

wherein
n is 1, 2 or 3;

each of R, $R_1$ and $R_2$, which may be the same or different, is hydrogen, halogen, hydroxy, cyano, $C_1$–$C_6$ alkyl, $CF_3$, $C_1$–$C_6$ alkoxy, $C_1$–$C_6$ alkylthio, formyl, $C_2$–$C_6$ alkanoyl, carboxy, $C_1$–$C_6$ alkoxy-carbonyl, nitro, —N ($R_4$ $R_5$) in which each of $R_4$ and $R_5$ independently is hydrogen, $C_1$–$C_6$ alkyl, formyl or $C_2$–$C_6$ alkanoyl; or a ($R_6$ $R_7$) N—$SO_2$ group, in which each of $R_6$ and R7 independently is hydrogen or $C_1$–$C_6$ alkyl;

$R_3$ is an imidazolyl group of formula

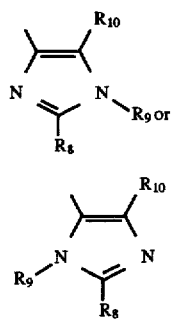

wherein each of $R_8$ and $R_{10}$ which may be the same or different is hydrogen or $C_1$–$C_6$ alkyl, $R_9$ is hydrogen, $C_1$–$C_6$ alkyl or a nitrogen protecting group; and the pharmaceutically acceptable salts thereof.

The formula reported above for the compounds according to the present invention includes all the possible isomers, in particular enantiomers, as well as their mixtures. The invention includes within its scope the metabolites and the metabolic precursors or bio-precursors (otherwise known as pro-drugs) of the compounds of formula (I). Namely the invention includes compounds which have a different formula to formula (I) above but which nevertheless upon administration to a human being are converted directly or indirectly in vivo into a compound of formula (I).

A halogen atom may be a fluorine, chlorine, bromine or iodine atom, preferably it is chlorine or bromine. The alkyl, alkoxy and alkylthio group may be a branched or straight chain group.

A $C_1$–$C_6$ alkyl group is preferably a $C_1$–$C_4$ alkyl group, e.g. methyl, ethyl, propyl, isopropyl, butyl, sec. butyl or tert. butyl, in particular methyl or ethyl.

A $C_1$–$C_6$ alkoxy group is preferably a $C_1$–$C_4$ alkoxy group e.g. methoxy, ethoxy, propoxy, isopropoxy and butoxy, preferably methoxy and ethoxy.

A $C_1$–$C_6$ alkylthio group is preferably a $C_1$–$C_4$ alkylthio group, e.g. methylthio, ethylthio, propylthio and butylthio, in particular methylthio.

A $C_2$–$C_6$ alkanoyl group is e.g. a $C_2$–$C_4$ alkanoyl group, in particular acetyl and propionyl.

A nitrogen protecting group may be one of those employed usually in the chemistry of peptides, typically triphenylmethyl, t-butyloxycarbonyl, benzyloxycarbonyl, acetyl, formyl, di(p-methoxyphenyl)methyl or (p-methoxyphenyl)diphenylmethyl.

Pharmaceutically acceptable salts of the compounds of formula (I) include acid addition salts, with inorganic acids, e.g. nitric, hydrochloric, hydrobromic, sulphuric, perchloric and phosphoric acid, or organic acids, e.g. acetic, propionic, glycolic, lactic, oxalic, malonic, fumaric, malic, maleic, tartaric, citric, benzoic, cinnamic, mandelic and salicylic acid.

Preferred compounds of the invention are the compounds of formula (I) wherein each of R, $R_1$ and $R_2$, which may be the same or different, is hydrogen, halogen, cyano, $CF_3$, $C_1$–$C_4$ alkyl, $C_1$–$C_4$ alkylthio, $C_1$–$C_4$ alkoxy or —N($R_4$ $R_5$) in which each of $R_4$ and $R_5$ independently is hydrogen, $C_1$–$C_4$ alkyl, formyl or $C_2$–$C_4$ alkanoyl;

n is 1 or 2;

$R_3$ is as defined above;

each of $R_8$, $R_9$ and $R_{10}$ is independently hydrogen or $C_1$–$C_4$ alkyl; and the pharmaceutically acceptable salts thereof.

Most preferred compounds of the invention are the compounds of formula (I) wherein each of R, $R_1$ and $R_2$, which may be the same or different, is hydrogen, halogen or $C_1$–$C_4$ alkyl;

n is 1;

$R_3$ is as defined above;

each of $R_8$ and $R_9$ is hydrogen and $R_{10}$ is $C_1$–$C_4$ alkyl; and the pharmaceutically acceptable salts thereof.

Examples of specific compounds according to the invention are the following:

2,3,3a,4-tetrahydro-2-(5-methyl-1H-imidazol-4-yl) methyl-1H-imidazo[5,1-c][1,4]benzoxazin-1-one;

2,3, 3a,4-tetrahydro-8-chloro-2-(5-methyl-1H-imidazol-4-yl)methyl-1H-imidazo[5,1-c][1,4]benzoxazin-1-one;

2,3,3a,4-tetrahydro-6-chloro-2-(5-methyl-1H-imidazol-4-yl)methyl-1H-imidazo[5,1-c][1,4]benzoxazin-1-one;

2,3,3a,4-tetrahydro-8-methyl-2-(5-methyl-1H-imidazol-4-yl)methyl-1H-imidazo[5, 1-c][1,4]benzoxazin-1-one;

2,3,3a,4-tetrahydro-6-methyl-2-(5-methyl-1H-imidazol-4-yl)methyl-1H-imidazo[5,1-c][1,4]benzoxazin-1-one;

2,3,3a,4-tetrahydro-6,8-dichloro-2-(5-methyl-1H-imidazol-4-yl)methyl-1H-imidazo[5,1-c][1,4]benzoxazin-1-one; and 2,3,3a,4-tetrahydro-6,8-dimethyl-2-(5-methyl-1H-imidazol-4-yl)methyl-1H-imidazo[5,1-c][1,4]benzoxazin-1-one; and the pharmaceutically acceptable salts thereof; in particular the hydrochloride.

The compounds of the invention and the salts thereof can be obtained by a process comprising:

a) reacting a compound of formula (II), or a salt thereof

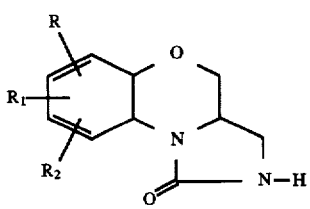

wherein R, $R_1$ and $R_2$ are as defined above with a compound of formula (III)

wherein n is as defined above, Y is a leaving group and in $R_3$, which is as defined above, $R_9$ is $C_1$–$C_6$ alkyl or a nitrogen protecting group, thus obtaining a compound of formula (I) wherein $R_9$ is as defined above bar hydrogen; or b) deprotecting a compound of formula (IV)

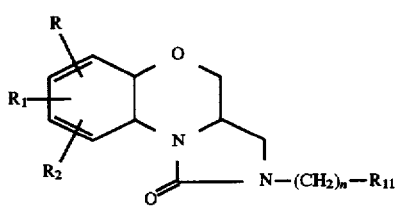

wherein R, $R_1$ and $R_2$ and n are as defined above and $R_{11}$ is a group of formula

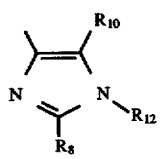

or

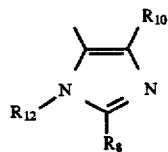

wherein $R_8$ and $R_{10}$ are as defined above and $R_{12}$ is a nitrogen protecting group, thus obtaining a compound of formula (I), wherein $R_9$ is hydrogen; and, if desired, converting a compound of formula (I) into another compound of formula (I), and/or, if desired, converting a compound of formula (I) into a pharmaceutically acceptable salt thereof, and/or, if desired, converting a salt of a compound of formula (I) into a free compound, and/or, if desired, separating a mixture of isomers of a compound of formula (I) into the single isomers.

A salt of a compound of formula (II) may be for example an alkali metal salt, preferably a sodium or potassium salt.

The salification of a compound of formula (II) may be performed according to known methods, e.g. by treatment with an alkaline hydride, preferably sodium hydride, or with lithium diisopropylamide or an alkaline alkoxide, preferably potassium tert-butylate.

In a compound of formula (III) Y as a leaving group may be for example an halogen atom, typically chlorine, iodine or bromine, in particular chlorine; or the residue of a reactive ester, typically the residue of a reactive ester of an alcohol, in particular a sulfonyloxy derivative e.g. a mesyloxy or tosyloxy, more preferably a mesyloxy group.

The reaction of a compound of formula (II), or a salt thereof, with a compound of formula (III) can be performed for instance in an anhydrous aprotic organic solvent e.g. dimethylformamide, dimethylacetamide or in other organic solvents e.g. toluene, tetrahydrofuran or dioxane, at temperatures ranging from about $-10°$ C. to reflux temperature, in the presence of a basic agent e.g. NaH or potassium tert-butylate.

The deprotection of a compound of formula (IV) can be carried out according to known methods, e.g. by acidic hydrolysis, for instance with an aqueous solution of hydrohalic acids, typically HCl or HBr, or diluted sulphuric acid, or aqueous acetic acid, at a temperature ranging from room temperature to reflux temperature.

Alternatively the same deprotection can be carried out by treatment with trifluoroacetic acid in an organic aprotic solvent, e.g. methylene chloride, chloroform or carbonium tetrachloride, at a temperature ranging from room temperature to reflux temperature.

A compound of formula (I) can be converted, if desired, into another compound of formula (I) according to known methods. Thus for instance a compound of formula (I), wherein one or more of R, $R_1$ and $R_2$ is amino, can be converted into another compound of formula (I) wherein one or more of R, $R_1$ and $R_2$ is $C_2$–$C_6$ alkanoylamino or formylamino.

A compound of formula (I) in which one or more of R, $R_1$ and $R_2$ is carboxy can be converted into another compound of formula (I) wherein one or more of R, $R_1$ and $R_2$ is $C_1$–$C_6$ alkoxycarbonyl, and vice versa. These optional conversions can be carried out by methods known in themselves.

A compound of formula (I), wherein $R_9$ is hydrogen, may be converted into another compound of formula (I), wherein $R_9$ is $C_1$–$C_6$ alkyl, by following well known procedures, for example as described above as to the reaction of a compound of formula (II) with an alkylating agent of formula (III).

A compound of formula (I), wherein one or more of R, $R_1$ and $R_2$ is hydroxy, may be converted into the respective compound of formula (I), wherein one or more of R, $R_1$ and $R_2$ is $C_1$–C6 alkoxy, by reaction with a suitable alkyl halide in the presence of a base such as NaOH, KOH, $Na_2CO_3$, $K_2CO_3$, NaH, $NaNH_2$, sodium methoxide or sodium ethoxide, in a solvent selected from the group consisting, for example, of methanol, ethanol, dioxane, acetone, dimethylformamide, hexamethylphosphoramide, tetrahydrofuran, water and their mixtures at a temperature ranging preferably between about 0° C. and about 70° C. Furthermore a compound of formula (I) wherein one or more of R, $R_1$ and $R_2$ is $C_1$–$C_6$ alkoxy may be converted into the respective compound of formula (I) wherein one or more of R, $R_1$ and $R_2$ is hydroxy, for example, by treatment with pyridine hydrochloride or with a strong acid such as HBr or HI, or with a Lewis acid such as $AlCl_3$ or $BBr_3$ or with an alkaline salt of a thiol.

Also the reduction of a compound of formula (I) wherein one or more of R, $R_1$ and $R_2$ is nitro into the corresponding compound of formula (I) wherein one or more of R, $R_1$ and $R_2$ is amino may be carried out by known procedures, e.g. by catalytic hydrogenation and using preferably Pd/C as catalyst.

Alkylation of a compound of formula (I), wherein one or more of R, $R_1$ and $R_2$ is amino, may be carried out, for example by reacting a suitable $C_1$–$C_6$ alkyl halide in the presence of a base such as $Na_2CO_3$, $K_2CO_3$, NaH or $NaNH_2$, in a solvent such as dimethylformamide, dimethylacetamide, dioxane, tetrahydrofuran or their mixtures, at a temperature varying between room temperature and about 100° C. Said alkylation process provides a mixture of N,N' dialkylated compounds of formula (I). The single alkylated compounds may be separated from the mixture according to well known methods, e.g. by silica gel column chromatography.

The optional salification of a compound of formula (I) as well as the conversion of a salt into the free compound and the separation of a mixture of isomers into the single isomers may be carried out by conventional methods.

For example the separation of a mixture of optical isomers into the individual isomers may be carried out by salification with an optically active acid and subsequent fractional crystallization or by chromatography, either column chromatography or high pressure liquid chromatography (HPLC).

When in the compounds described above groups are present which need to be protected during the reactions described above, such groups can be protected in a conventional way before the reaction takes place and then deprotected. Examples of protecting groups are those employed usually in the chemistry of peptides.

The compounds of formula (II) are either known or may be obtained according to known methods e.g. as described in J. Heterocyclic Chem., 20, 139 (1983).

The compounds of formula (III) are known or may be obtained by known methods.

PHARMACOLOGY

The compounds of the invention are active on the serotoninergic system, in particular as $5HT_3$ receptor antagonist, as proven for example by the fact that they have been found to be active in antagonizing the von Bezold-Jarisch chemoreflex evoked by 5-HT in the anesthetised rat according to the method described by Fozard J. R., Naunyn-Schmiedeberg's Arch. Pharmacol. 326, 36–44 (1984).

Following Table I summarizes the activity data obtained for two representative compounds of the invention.

TABLE I

Inhibition of the von Bezold-Jarisch reflex elicited by 5-HT (30 µg/kg i.v.) by FCE compounds in the anesthetized rat. Values are mean ± in S.E.M. from N animals

| Compound | Dose (µg/kg i.v.) | N | % inhibition | $ED_{50}$ (50 µg/kg) (limits) |
|---|---|---|---|---|
| FCE 28158 | 100 | 6 | 82 | 23.6 (18.0–29.7) |
| FCE 28609 | 100 | 6 | 97.5 | 8.18 (6.31–10.4) |
| Vehicle | | | 4.42 ± 2.91 | |

* P<0.01 vs controls (Dunnett's tests)
N = number of animals

The compounds of the invention have also been found to be potent and selective inhibitors of the binding of $^3$H-BRL 43694 as described by Nelson D. R. and Thomas D. R., [$^3$H]-BRL 43694 (Granisetron) is a specific ligand for 5-$HT_3$ binding sites in rat brain cortical membranes: Biochem. Pharmac. 38, 1693–1695, 1989.

The following Table II summarizes the activity data obtained in this in-vitro test for two representative compounds of the invention in comparison with compound A, i.e. a close chemically related compound falling within U.S. Pat. No. 4,134,974.

TABLE II

5-$HT_3$ binding affinity for rat entorhinal cortex

| Compound | $^3$H-BRL 43694 $IC_{50}$, nM |
|---|---|
| FCE 28158 | 76 |
| FCE 28609 | 6 |
| Compound A | 1210 |

In the tables:
FCE 28158 means:
2,3,3a,4-tetrahydro-2-(5-methyl-1H-imidazol-4-yl)methyl-1H-imidazo[5,1-c][1,4]benzoxazin-1-one;
FCE 28609 means:
2,3,3a,4-tetrahydro-8-chloro-2-(5-methyl-1H-imidazol-4-yl)methyl-1H-imidazo[5,1-c][1,4]benzoxazin-1-one;
Compound A means:
2,3,3a,4-tetrahydro-2-[2-(2-methyl-imidazol-1-yl)ethyl]-1H-imidazo[5,1-c][1,4]benzoxazin-1-one hydrochloride.

In view of said activity, the compounds of the present invention can be useful, for example, in the treatment of CNS disorders such as, e.g., anxiety and psychosis, and/or in the treatment of gut motility disorders, and/or emesis.

In view of the above activity, the compounds of the invention can be also useful as, for example, anti-migraine or anti-drug addiction agents, or as cognition activators.

The dosage level suitable for administration to adult humans of the compounds of the invention, either for prophylaxis or therapeutic treatment, may range from about 0.010 to about 20 mg/kg of body weight, depending on the chosen route of administration, on the particular compound chosen, on the particular patient under treatment and also on the nature and severity of the disorder.

For instance, the compound of the invention 2,3,3a,4-tetrahydro-8-chloro-2-(5-methyl-1H-imidazol-4-yl)methyl-1H-imidazo[5,1-c][1,4]benzoxazin-1-one is suitable administered orally at a dosage in this range.

Preferably the compounds may be, e.g., administered in single or divided doses such that the total daily dosage falls within the range of about 0.020 to about 10 mg/kg per day.

Of course, these dosage regimens may be adjusted to provide the optimal therapeutic response.

The compounds of the invention can be administered in a variety of dosage forms, e.g. orally, in the form of tablets, capsules, sugar- or film-coated tablets, liquid solutions or suspensions.

The invention includes pharmaceutical compositions comprising a compound of the invention in association with a pharmaceutically acceptable excipient (which can be a carrier or diluent).

The nature of the pharmaceutical compositions containing the compounds of this invention in association with pharmaceutically acceptable carriers or diluents will, of course, depend upon the desired route of administration. The compositions may be formulated in the conventional manner with the usual ingredients. For example, the compounds of the invention may be administered in the form of aqueous or oily solutions, or suspensions, tablets, pills, gelatine capsules, syrups, drops or suppositories.

Thus, for oral administration, the pharmaceutical composition containing the compounds of this invention are preferably tablets, pills or gelatine capsules which contain the active substance together with diluents, such as lactose, dextrose, sucrose, mannitol, sorbitol, cellulose; lubricants, for instance silica, talc, stearic acid, magnesium or calcium stearate, and/or polyethylene glycols; or they may also contain binders, such as starches, gelatine, methylcellulose, carboxymethylcellulose, gum-arabic, tragacanth, polyvinylpyrrolidone; disaggregating agents, such as starches, alginic acid, alginates, sodium starch glycolate; effervescing mixtures; dyestuffs; sweeteners; wetting agents, such as lecithin, polysorbates, laurylsulphates; and in general, non-toxic and pharmacologically inactive substances used in pharmaceutical formulations. Said pharmaceutical preparations may be manufactured in known manner, for example by means of mixing, granulating, tabletting, sugar-coating, or film-coating processes. The liquid dispersions for oral administration may be e.g. syrup, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate; glycols, e.g. propylene glycol, and if desired, a suitable amount of lidocaine hydrochloride.

The solutions for intravenous injection or infusion may contain as carrier, for example, sterile water or preferably they may be in the form of sterile aqueous isotonic saline solutions.

The suppositories may contain together with the active compound a pharmaceutically acceptable carrier e.g. cocoa-butter, polyethylene glycol, a polyoxyethylene sorbitan fatty acid ester surfactant or lecithin.

The following examples illustrate but do not limit the present invention.

EXAMPLE 1

2,3,3a,4-tetrahydro-2-(5-methyl-1-triphenylmethyl-1H-imidazol-4-yl)methyl-1H-imidazo[5, 1-c] [1,4]benzoxazin-1-one.

To a stirred solution of 2,3,3a,4-tetrahydro-1H-imidazo[5,1-c][1,4]benzoxazin-1-one (0.89 g; 0.0047 moles) in 20 ml of anhydrous dimethylformamide kept under nitrogen atmosphere, 50% NaH (0.22 g; 0.0047 moles) is added. The solution is stirred for 1 hour at 60° C.; then, at room temperature, 4-chloromethyl-5-methyl-1-triphenylmethyl-1H-imidazole (1.75 g; 0.0047 moles) is added. The mixture is stirred for 6 hours at 70° C., then cooled, poured into water and extracted with methylene chloride.

The organic layer is washed with brine, dried over anhydrous sodium sulfate and, after filtration, evaporated to dryness. The residue is purified by silica gel flash-chromatography (ethyl acetate as eluant) to give 1.5 g of the title product as a amorphous solid;

$C_{34}H_{30}N_4O_2$, required=C 77.54 H 5.74 N 10.64 found=C 77.90 H 6.03 N 10.18

By proceeding analogously, the following compounds can be prepared:

2,3,3a,4-tetrahydro-8-chloro-2-(5-methyl-1-triphenylmethyl-1H-imidazol-4-yl)methyl-1H-imidazo[5, 1-c] [1,4]benzoxazin-1-one;

2,3,3a,4-tetrahydro-8-methyl-2-(5-methyl-1-triphenylmethyl-1H-imidazol-4-yl)methyl-1H-imidazo[5, 1-c] [1,4]benzoxazin-1-one;

2,3,3a,4-tetrahydro-6-chloro-2-(5-methyl-1-triphenylmethyl-1H-imidazol-4-yl)methyl-1H-imidazo[5, 1-c] [1,4]benzoxazin-1-one;

2,3,3a,4-tetrahydro-6-methyl-2-(5-methyl-1-triphenylmethyl-1H-imidazol-4-yl)methyl-1H-imidazo[5, 1-c] [1,4]benzoxazin-1-one;

2,3,3a,4-tetrahydro-6,8-dichloro-2-(5-methyl-1-triphenylmethyl-1H-imidazol-4-yl)methyl-1H-imidazo[5,1-c][1,4]benzoxazin-1-one;

2,3,3a,4-tetrahydro-6,8-dimethyl-2-(5-methyl-1-triphenylmethyl-1H-imidazol-4-yl)methyl-1H-imidazo[5,1-c][1,4]benzoxazin-1-one; and 2,3,3a,4-tetrahydro-2-(1,5-dimethyl-1H-imidazol-4-yl)methyl-1H-imidazo[5,1-c][1,4]benzoxazin-1-one.

EXAMPLE 2

2,3,3a,4-tetrahydro-2-(5-methyl-1H-imidazol-4-yl)methyl-1H-imidazo[5,1-c][1,4]benzoxazin-1-one.

A solution of 2,3,3a,4-tetrahydro-2-(5-methyl-1-triphenylmethyl-1H-imidazol-4-yl)methyl-1H-imidazo[5,1-c]-[1,4]benzoxazin-1-one (0.63 g; 0.0012 moles) in acetic acid (15 ml), water (15 ml) and tetrahydrofuran (15 ml) is heated at reflux for 2 hours. The solution is cooled and poured into 1N hydrochloric acid (50 ml) and washed with ethyl acetate.

The aqueous layer is basified with potassium carbonate to about pH 9 and extracted with methylene chloride. The organic layer is washed with brine, dried over anhydrous sodium sulfate and, after filtration, evaporated to dryness. The residue is triturated with dry diethyl ether to give 0.27 g of the title product as a white solid; m.p. 212°–215.5° C.;

$C_{15}H16N_4O_2$ required=C 63.36 H 5.67 N 19.71 found=C 62.93 H 5.64 N 19.64

By proceeding analogously, the following compounds can be prepared:

2,3,3a,4-tetrahydro-8-chloro-2-(5-methyl-1H-imidazol-4-yl)methyl-1H-imidazo[5,1-c][1,4]benzoxazin-1-one, m.p. 240°–264.5° C.;

2,3,3a,4-tetrahydro-8-methyl-2-(5-methyl-1H-imidazol-4-yl)methyl-1H-imidazo[5,1-c][1,4]benzoxazin-1-one;

2,3,3a,4-tetrahydro-6-chloro-2-(5-methyl-1H-imidazol-4-yl)methyl-1H-imidazo[5,1-c][1,4]benzoxazin-1-one;

2,3,3a,4-tetrahydro-6-methyl-2-(5-methyl-1H-imidazol-4-yl)-methyl-1H-imidazo[5,1-c][1,4]benzoxazin-1-one;

2,3,3a,4-tetrahydro-6,8-dichloro-2-(5-methyl-1H-imidazol-4-yl)methyl-1H-imidazo[5,1-c][1,4]benzoxazin-1-one; and 2,3,3a,4-tetrahydro-6,8-dimethyl-2-(5-methyl-1H-imidazol-4-yl)-methyl-1H-imidazo[5,1-c][1,4]benzoxazin-1-one.

EXAMPLE 3

2,3,3a,4-tetrahydro-2-(5-methyl-1H-imidazol-4-yl)methyl-1H-imidazo[5,1-c][1,4]benzoxazin-1-one hydrochloride.

To a solution of 2,3,3a,4-tetrahydro-2-(5-methyl-1H-imidazol-4-yl)methyl-1H-imidazo[5, 1-c] [1,4]benzoxazin-1-one (0.5 g; 0.00176 moles) in absolute ethanol (10 ml), an excess of a solution of hydrochloric acid is added. Diethyl ether is added, the precipitate is filtered to give 0.52 g of the title product as a white solid.

By proceeding analogously, the following compounds can be prepared:

2,3,3a,4-tetrahydro-8-chloro-2-(5-methyl-1H-imidazol-4-yl)methyl-1H-imidazo[5,1-c] [1,4] benzoxazin-1-one hydrochloride;

2,3,3a,⁴-tetrahydro-8-methyl-2-(5-methyl-1H-imidazol-4-yl)methyl-1H-imidazo[5,1-c][1,4]benzoxazin-1-one hydrochloride;

2,3,3a,4-tetrahydro-6-chloro-2-(5-methyl-1H-imidazol-4-yl)methyl-1H-imidazo[5,₁-c][1,4]benzoxazin-1-one hydrochloride;

2,3,3a,⁴-tetrahydro-6-methyl-2-(5-methyl-1H-imidazol-4-yl)methyl-1H-imidazo[5, 1-c] [1,4]benzoxazin-1-one hydrochloride;

2,3,3a,4-tetrahydro-6,8-dichloro-2-(5-methyl-1H-imidazol-4-yl)methyl-1H-imidazo [5,1-c][1,4]benzoxazin-1-one hydrochloride; and 2,3,3a, 4-tetrahydro-6,8-dimethyl-2-(5-methyl-1H-imidazol-4-yl)methyl-1H-imidazo[5,1-c][1,4]benzoxazin-1-one hydrochloride.

EXAMPLE 4

Tablets each weighing 150 mg and containing 60 mg of the active substance can be manufactured by blending and compressing the following ingredients:

| | |
|---|---|
| 2,3,3a,4-tetrahydro-8-chloro-2-(5-methyl-1H-imidazol-4-yl)methyl-1H-imidazo[5,1-c][1,4]benzoxazin-1-one | 60 mg |
| Starch | 50 mg |
| Cellulose microcrystalline | 30 mg |
| Polyvinylpyrrolidone | 5 mg |
| Sodium carboxymethyl starch | 4.5 mg |
| Magnesium stearate | 0.5 mg |

EXAMPLE 5

Capsules, each dosed at 200 mg and containing 80 mg of the active substance, can be prepared as follows:

| | |
|---|---|
| 2,3,3a,4-tetrahydro-8-chloro-2-(5-methyl-1H-imidazol-4-yl)methyl-1H-imidazo[5,1-c][1,4]benzoxazin-1-one | 80 mg |
| Corn starch | 60 mg |
| Cellulose microcrystalline | 59 mg |
| Magnesium stearate | 1 mg |

This formulation can be encapsulated in two-piece hard gelatin capsules and dosed at 200 mg for each capsule.

We claim:

1. A compound having formula (I)

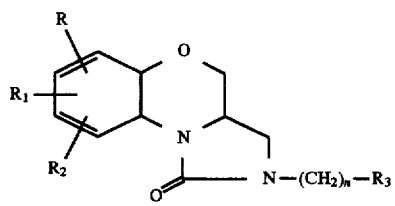

wherein n is 1, 2 or 3;

each of R, $R_1$, and $R_2$, which may be the same or different, is hydrogen, halogen, hydroxy, cyano, $C_1$–$C_6$ alkyl, $CF_3$, $C_1$–$C_6$ alkoxy, $C_1$–$C_6$ alkylthio, formyl, $C_2$–$C_6$ alkanoyl, carboxy, $C_1$–$C_6$ alkoxycarbonyl, nitro, —N($R_4R_5$) in which each of $R_4$ and $R_5$ independently is hydrogen, $C_1$–$C_6$ alkyl, formyl or $C_2$–$C_6$ alkanoyl; or a ($R_6R_7$)N—$SO_2$ group, in which each of $R_6$ and $R_7$ independently is hydrogen or $C_1$–$C_6$ alkyl;

$R_3$ is an imidazolyl group of formula

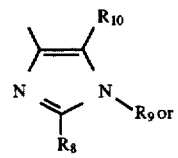

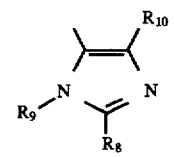

wherein each of $R_8$ and $R_{10}$ which may be the same or different is hydrogen or $C_1$–$C_6$ alkyl, $R_9$ is hydrogen, $C_1$–$C_6$ alkyl or a nitrogen protecting group; and the pharmaceutically acceptable salts thereof.

2. A compound of formula (I), according to claim 1, wherein each of R, $R_1$ and $R_2$, which may be the same or different, is hydrogen, halogen, cyano, $CF_3$, $C_1$–$C_4$ alkyl, $C_1$–$C_4$ alkylthio, $C_1$–$C_4$ alkoxy or —N($R_4R_5$) in which each of $R_4$ and $R_5$ independently is hydrogen, $C_1$–$C_4$ alkyl, formyl or $C_2$–$C_4$ alkanoyl;

n is 1 or 2;

$R_3$ is as defined in claim 1;

each of $R_8$, $R_9$ and $R_{10}$ is independently hydrogen or $C_1$–$C_4$ alkyl; and the pharmaceutically acceptable salts thereof.

3. A compound of formula (I), according to claim 1 wherein each of R, $R_1$ and $R_2$ which may be the same or different, is hydrogen, halogen or $C_1$–$C_4$ alkyl;

n is 1;

$R_3$ is as defined in claim 1;

each of $R_8$ and $R_9$ is hydrogen and $R_{10}$ is $C_1$–$C_4$ alkyl;

and the pharmaceutically acceptable salts thereof.

4. A compound selected from the group consisting of 2,3,3a,4-tetrahydro-2-(5-methyl-1H-imidazol-4-yl)methyl-1H-imidazo[5,1-c][1,4]benzoxazin-1-one;

2,3,3a,4-tetrahydro-8-chloro-2-(5-methyl-1H-imidazol-4-yl)methyl-1H-imidazo[5,1-c][1,4] benzoxazin-1-one;

2,3,3a,4-tetrahydro-6-chloro-2-(5-methyl-1H-imidazol-4-yl)methyl-1H-imidazo[5,1-c][1,4] benzoxazin-1-one;

2,3,3a,4-tetrahydro-8-methyl-2-(5-methyl-1H-imidazol-4-yl)methyl-1H-imidazo[5,1-c][1,4] benzoxazin-1-one;

2,3,3a,4-tetrahydro-6-methyl-2-(5-methyl-1H-imidazol-4-yl)methyl-1H-imidazo[5,1-c][1,4] benzoxazin-1-one;

2,3,3a,4-tetrahydro-6,8-dichloro-2-(5-methyl-1H-imidazol-4-yl)methyl-1H-imidazo[5,1-c][1,4]benzoxazin-1-one;

2,3,3a,4-tetrahydro-6,8-dimethyl-2-(5-methyl-1H-imidazol-4-yl)methyl-1H-imidazo[5,1-c][1,4]benzoxazin-1-one;

or a pharmaceutically acceptable salt thereof.

5. The salt of a compound according to claim 4, wherein said salt is the hydrochloride.

6. A pharmaceutical composition comprising a suitable carrier and/or diluent and, as an active principle, a compound of formula (I) or a pharmaceutically acceptable salt thereof as defined in claim 1.

* * * * *